United States Patent [19]
Wang et al.

[11] Patent Number: 5,939,307
[45] Date of Patent: Aug. 17, 1999

[54] **STRAINS OF *ESCHERICHIA COLI*, METHODS OF PREPARING THE SAME AND USE THEREOF IN FERMENTATION PROCESSES FOR L-THREONINE PRODUCTION**

[75] Inventors: Ming-Der Wang, San Diego, Calif.; Jill S. Bradshaw; Stacia L. Swisher, both of Decatur, Ill.; Hungming James Liaw, Champaign, Ill.; Paul D. Hanke, Urbana, Ill.; Thomas P. Binder, Decatur, Ill.

[73] Assignee: The Archer-Daniels-Midland Company, Decatur, Ill.

[21] Appl. No.: 08/902,336

[22] Filed: Jul. 29, 1997

Related U.S. Application Data

[60] Provisional application No. 60/022,407, Jul. 30, 1996.

[51] Int. Cl.$^6$ ............................... C12N 1/20; C12P 13/08
[52] U.S. Cl. .................. 435/252.33; 435/115; 435/252.3
[58] Field of Search ........................... 435/252.3, 252.33, 435/115

[56] References Cited

U.S. PATENT DOCUMENTS

| | | | |
|---|---|---|---|
| 3,375,173 | 3/1968 | Nishimura et al. | 195/29 |
| 3,580,810 | 5/1971 | Shiio et al. | 195/29 |
| 3,582,471 | 6/1971 | Shiio et al. | 195/30 |
| 3,622,453 | 11/1971 | Akeyama et al. | 195/29 |
| 3,647,628 | 3/1972 | Nakayama et al. | 195/29 |
| 3,684,653 | 8/1972 | Abe et al. | 195/28 |
| 3,684,654 | 8/1972 | Nakayama et al. | 195/29 |

(List continued on next page.)

FOREIGN PATENT DOCUMENTS

| | | |
|---|---|---|
| 0 593 792 A1 | 4/1994 | European Pat. Off. . |
| 0 685 555 A1 | 12/1995 | European Pat. Off. . |
| 53-101591 | 9/1978 | Japan . |
| 258 753 | 10/1995 | Taiwan . |

OTHER PUBLICATIONS

Saint Girons et al. (1985) Evidence for an internal promoter in the *Escherichia coli* threonine operator, Journal of Bacteriology 161(1): 461–462, Jan. 1985.

Gardner et al. (1975) Operator–promoter functions in the threonine operon of *Escherichia coli*, Journal of Bacteriology 124(1): 161–166, Oct. 1975.

Chan et al. (1993) Amplification of the trytophan operon gene in *Escherichia coli* chromosome to increase L–tryptophan biosynthesis, Applied Microbiology and Biotechnology 40(2/3): 301–305, Nov. 1993.

Little, S., et al., "Translational Coupling in the Threonine Operon of *Escherichia coli* K–12," *J. Bacteriol.* 171(6):3518–3522 (1989).

Mizukami, T., et al., "Improvement of the Stability of Recombinant Plasmids Carrying the Threonine Operon in an L–Threonine–hyperproducing Strain of *Escherichia coli* W," *Agric. Biol. Chem.* 50(4):1019–1027 (1986).

English language abstract of Taiwanese Patent Publication No. 258 753, Derwent World Patents Index Accession No. 95–392096.

International Search Report for International Application No. PCT/US97/13359.

Burr, B. et al., "Homoserine Kinase from *Escherichia coli* K12," *Eur. J. Biochem.* 62:519–526 (1976).

Cohen, G.N., "The Common Pathway to Lysine, Methionine, and Threonine," In: *Amino Acids: Biosynthesis and Genetic Regulation,* Herrmann, K.M. and Somerville, R.L., eds., Addison–Wesley Publ. Co., Reading, MA, publ., pp. 147–171 (1983).

Falcoz–Kelly, F. et al., "The Methionine–Repressible Homoserine Dehydrogenase and Aspartokinase Activities of *Escherichia coli* K 12," *Euro. J. Biochem.* 8:146–152 (1969).

Freundlich, M., "Multivalent Repression in the Biosynthesis of Threonine in *Salmonella Typhimurium* and *Escherichia Coli*," *Biochem. Biophys. Res. Comm.* 10(3):277–282 (1963).

Gardner, J.F., "Regulation of the threonine operon: Tandem threonine and isoleucine codons in the control region and translational control of transcription termination," *Proc. Natl. Acad. Sci. USA* 76(4):1706–1710 (1979).

Johnson, E.J. et al., "Threonyl–Transfer Ribonucleic Acid Synthetase and the Regulation of the Threonine Operon in *Escherichia coli,*" *J. Bacteriology* 129(1):66–70 (1977).

Masuda, M. et al., "Improvement of Nitrogen Supply for L–Threonine Production by a Recombinant Strain of *Serratia marcescens,*" *Appl. Biochem. Biotech.* 37:255–265 (1992).

Miwa, K. et al., "Construction of L–Threonine Overproducing Strains of *Escherichia coli* K–12 Using Recombinant DNA Techniques," *Agric. Biol. Chem.* 47(10):2329–2334 (1983).

Nass, G. et al., "Effect of the Antibiotic Borrelidin on the Regulation of Threonine Biosynthetic Enzymes in *E. Coli,*" *Biochem. Biophys. Res. Comm.* 34(1):84–91 (1969).

Nass, G. and J. Thomale, "Alteration of Structure or Level of Threonyl–tRNA–Synthetase in Borrelidin Resistant Mutants of *E. Coli,*" *FEBS Letters* 39(2):182–186 (1974).

(List continued on next page.)

*Primary Examiner*—Robert A. Wax
*Assistant Examiner*—Einar Stole
*Attorney, Agent, or Firm*—Sterne, Kessler, Goldstein & Fox P.L.L.C.

[57] ABSTRACT

The present invention relates to novel strains of *Escherichia coli* and fermentation processes involving these microorganisms. More specifically, the present invention relates to genetically-modified *Escherichia coli* strains and the use thereof for the production of the amino acids, particularly members of the aspartate family of amino acids such as threonine. The present invention also relates to methods of preparing *E. coli* strains for use in the fermentative production of amino acids.

20 Claims, 5 Drawing Sheets

U.S. PATENT DOCUMENTS

| | | |
|---|---|---|
| 3,711,375 | 1/1973 | Nakayama et al. .................. 195/29 |
| 3,732,144 | 5/1973 | Nakayama et al. .................. 195/29 |
| 4,321,325 | 3/1982 | Debabov et al. ................... 435/115 |
| 4,347,318 | 8/1982 | Miwa et al. ....................... 435/115 |
| 4,371,615 | 2/1983 | Miwa et al. ....................... 435/115 |
| 4,452,890 | 6/1984 | Tsuchida et al. .................. 435/115 |
| 4,463,094 | 7/1984 | Chibata et al. .................... 435/115 |
| 4,601,983 | 7/1986 | Nakamori et al. ................. 435/115 |
| 4,757,009 | 7/1988 | Sano et al. ........................ 435/106 |
| 4,945,058 | 7/1990 | Yanai et al. ..................... 435/252.3 |
| 4,946,781 | 8/1990 | Nakamori et al. ................. 435/115 |
| 4,980,285 | 12/1990 | Sano et al. ........................ 435/108 |
| 4,996,147 | 2/1991 | Furukawa et al. ................. 435/115 |
| 5,017,483 | 5/1991 | Furukawa et al. ................. 435/115 |
| 5,019,503 | 5/1991 | Terasawa et al. .................. 435/115 |
| 5,077,207 | 12/1991 | Shiio et al. ........................ 435/115 |
| 5,087,566 | 2/1992 | Takano et al. ..................... 435/115 |
| 5,098,835 | 3/1992 | Yamada et al. .................... 435/115 |
| 5,153,123 | 10/1992 | Terasawa et al. .................. 435/115 |
| 5,164,307 | 11/1992 | Yoshihara et al. ................. 435/106 |
| 5,175,107 | 12/1992 | Debabov et al. ............... 435/252.33 |
| 5,188,949 | 2/1993 | Tsuchida et al. .................. 435/115 |
| 5,217,883 | 6/1993 | Anazawa et al. .................. 435/115 |
| 5,236,831 | 8/1993 | Katsumata et al. ................ 435/106 |
| 5,264,353 | 11/1993 | Yamada et al. .................... 435/115 |
| 5,342,766 | 8/1994 | Yamada et al. .................... 435/115 |
| 5,376,538 | 12/1994 | Kino et al. ......................... 435/115 |
| 5,474,918 | 12/1995 | Kino et al. ......................... 435/115 |
| 5,631,157 | 5/1997 | Debabov et al. ............... 435/252.33 |
| 5,705,371 | 1/1998 | Debabov et al. ................... 435/115 |

OTHER PUBLICATIONS

Parsot, C. et al., "Nucleotide sequence of thrC and of the transcription termination region of the threonine operon in *Escherichia coli* K12," *Nucl. Acids Res.* 11(21):7331–7345 (1983).

Patte, J.–C. et al., "Regulation by Methionine of the Synthesis of a Third Aspartokinase and of a Second Homoserine Dehydrogenase in *Escherichia Coli* $K_{12}$," *Biochim. Biophys. Acta* 136:245–257 (1967).

Shimizu, E. et al., "Culture Conditions for Improvement of L–Threonine Production Using a Genetically Self–cloned L–Threonine Hyperproducing Strain of *Escherichia coli* K–12," *Biosci. Biotech. Biochem.* 59(6):1095–1098 (Jun. 1995).

Thèze, J. et al., "Mapping of the Structural Genes of the Three Aspartokinases and of the Two Homoserine Dehydrogenases of *Escherichia coli* K–12," *J. Bacteriology* 117(1):133–143 (1974).

Thèze, J. and I. Saint–Girons, "Threonine Locus of *Escherichia coli* K–12: Genetic Structure and Evidence for an Operon," *J. Bacteriology* 118(3):990–998 (1974).

Truffa–Bachi, P. et al., "The Threonine–Sensitive Homoserine Dehydrogenase and Aspartokinase Activities of *Escherichia coli* K12," *Euro. J. Biochem.* 5:73–80 (1968).

English Language abstract of JP 53–101591, Derwent Accession No. 78–73642A/197841.

STRAINS OF *ESCHERICHIA COLI*, METHODS OF PREPARING THE SAME AND USE THEREOF IN FERMENTATION PROCESSES FOR L-THREONINE PRODUCTION

This application claims the benefit of the filing date of provisional application No. 60/022,407, filed Jul. 30, 1996.

FIELD OF THE INVENTION

The present invention relates to novel strains of *Escherichia coli* and fermentation processes involving these microorganisms. More specifically, the present invention relates to genetically-modified *Escherichia coli* strains and the use thereof for the production of the amino acids, particularly members of the aspartate family of amino acids such as threonine. The present invention also relates to methods of preparing *E. coli* strains for use in the fermentative production of amino acids.

BACKGROUND OF THE INVENTION

In *Escherichia coli*, the amino acids L-threonine, L-isoleucine, L-lysine and L-methionine derive all or part of their carbon atoms from aspartate (aspartic acid) via the following common biosynthetic pathway (G. N. Cohen, "The common pathway to lysine, methionine and threonine," pp. 147–171 in *Amino Acids: Biosynthesis and Genetic Regulation*, K. M. Herrmann and R. L. Somerville, eds., Addison-Welesley Publishing Co., Inc., Reading, Mass. (1983)):

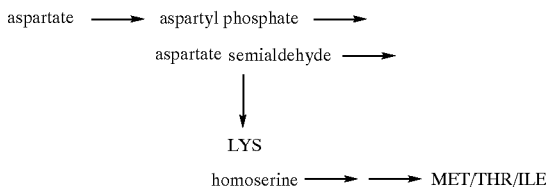

The first reaction of this common pathway is catalyzed by one of three distinct aspartate kinases (AK I, II, or III), each of which is encoded by a separate gene and differs from the others in the way its activity and synthesis are regulated. Aspartate kinase I, for example, is encoded by thrA, its activity is inhibited by threonine, and its synthesis is repressed by threonine and isoleucine in combination. AK II, however, is encoded by metL and its synthesis repressed by methionine (although its activity is not inhibited by methionine or by paired combinations of methionine, lysine, threonine and isoleucine (F. Falcoz-Kelly et al., *Eur. J. Biochem.* 8:146–152 (1969); J. C. Patte et al., *Biochim. Biophys. Acta* 136:245–257 (1967)). AK III is encoded by lysC and its activity and synthesis are inhibited and repressed, respectively, by lysine.

Two of the AKs, I and II, are not distinct proteins, but rather a domain of a complex enzyme that includes homoserine dehydrogenase I or II, respectively, each of which catalyzes the reduction of aspartate semialdehyde to homoserine (P. Truffa-Bachi et al., *Eur. J. Biochem.* 5:73–80 (12968)). Homoserine dehydrogenase I is therefore also encoded by thrA, its synthesis is repressed by threonine plus isoleucine and its activity is inhibited by threonine. HD II is similarly encoded by metL and its synthesis is repressed by methionine.

Threonine biosynthesis includes the following additional reactions: homoserine→homoserine phosphate→threonine.

The phosphorylation of homoserine is catalyzed by homoserine kinase, a protein which consists of two identical 29 kDa subunits encoded for by thrB and whose activity is inhibited by threonine (B. Burr et al., *J. Biochem.* 62:519–526 (1976)). The final step, the complex conversion of homoserine phosphate to L-threonine is catalyzed by threonine synthase, a 47 kDa protein encoded for by thrC (C. Parsot et al., *Nucleic Acids Res.* 11:7331–7345 (1983)).

The thrA, thrB and thrC genes all belong to the thr operon, a single operon located at 0 minutes on the genetic map of *E. coli* (J. Thèze and I. Saint-Girons, *J. Bacteriol.* 118:990–998 (1974); J. Thèze et al., *J. Bacteriol.* 117:133–143 (1974)). These genes encode, respectively, for aspartate kinase I-homoserine dehydrogenase I, homoserine kinase and threonine synthase. Biosynthesis of these enzymes is subject to multivalent repression by threonine and isoleucine (M. Freundlich, *Biochem. Biophys. Res. Commun.* 10:277–282 (1963)).

A regulatory region is found upstream of the first structural gene in the thr operon and its sequence has been determined (J. F. Gardner, *Proc. Natl. Acad. Sci. USA* 76:1706–1710 (1979)). The thr attenuator, downstream of the transcription initiation site, contains a sequence encoding a leader peptide; this sequence includes eight threonine codons and four isoleucine codons. The thr attenuator also contains the classical mutually exclusive secondary structures which permit or prevent RNA polymerase transcription of the structural genes in the thr operon, depending on the levels of the charged threonyl- and isoleucyl-tRNAs.

Because of the problems associated with obtaining high levels of amino acid production via natural biosynthesis (e.g. repression of the thr operon by the desired product), bacterial strains have been produced having plasmids containing a thr operon with a thrA gene that encodes a feedback-resistant enzyme. With such plasmids, L-threonine has been produced on an industrial scale by fermentation processes employing a wide variety of microorganisms, such as *Brevibacterium flavum, Serratia marcescens,* and *Escherichia coli*.

For example, the *E. coli* strain BKIIM B-3996 (Debabov et al., U.S. Pat. No. 5,175,107), which contains the plasmid pVIC40, makes about 85 g/L in 36 hr. The host is a threonine-requiring strain because of a defective threonine synthase. In BKIIM B-3996, it is the recombinant plasmid, pVIC40, that provides the crucial enzymatic activities, i.e, a feedback-resistant AK I-HD I, homoserine kise and threonine synthase, needed for threonine biosynthesis. This plasmid also complements the host's threonine auxotrophy.

*E. coli* strain 294 (E. Shimizu et al., *Biosci. Biotech. Biochem.* 59:1095–1098 (1995)) is another example of a recombinant *E. coli* threonine producer. Strain 294 was constructed by cloning the thr operon of a threonine-overproducing mutant strain, *E. coli* K-12 (βIM4) (derived from *E. coli* strain ATCC 21277), into plasmid pBR322, which was then introduced into the parent strain (K. Wiwa et al., *Agric. Biol. Chem.* 47:2329–2334 (1983)). Strain 29-4 produces about 65 g/L of L-threonine in 72 hr.

Similarly constructed recombinant strains have been made using other organisms. For example, the *S. marcescens* strain T2000 contains a plasmid having a thr operon which encodes a feedback-resistant thrA gene product and produces about 100 g/L of threonine in 96 hrs (M. Masuda et al., *Applied Biochemistry and Biotechnology* 37:255–262 (1992). All of these strains contain plasmids having multiple copies of the genes encoding the threonine biosynthetic enzymes, which allows overexpression of these enzymes.

This overexpression of the plasmid-borne genes encoding threonine biosynthetic enzymes, particularly a thrA gene encoding a feedback-resistant AK I-HD I, enables these strains to produce large amounts of threonine. Other examples of plasmid-containing microorganisms are described, for example, in U.S. Pat. Nos. 4,321,325; 4,347,318; 4,371,615; 4,601,983; 4,757,009; 4,945,058; 4,946,781; 4,980,285; 5,153,123; and 5,236,831.

Plasmid-containing strains such as these, however, have problems that limit their usefulness for commercial fermentative production of amino acids. For example, a significant problem with these strains is ensuring that the integrity of the plasmid-containing strain is maintained throughout the fermentation process because of potential loss of the plasmid during cell growth and division. To avoid this problem, it is necessary to selectively eliminate plasmid-free cells during culturing, such as by employing antibiotic resistance genes on the plasmid. This solution, however, necessitates the addition of one or more antibiotics to the fermentation medium, which is not commercially practical for large scale fermentations.

Another significant problem with plasmid-containing strains is plasmid stability. High expression of enzymes whose genes are coded on the plasmid, which is necessary for commercially practical fermentative processes, often brings about plasmid instability (E. Shimizu et al., *Biosci. Biotech. Biochem.* 59:1095–1098 (1995)). Plasmid stability is also dependent upon factors such as cultivation temperature and the level of dissolved oxygen in the culture medium. For example, plasmid-containing strain 29-4 was more stable at lower cultivation temperatures (30° C. vs. 37° C.) and higher levels of dissolved oxygen (E. Shimizu et al., *Biosci. Biotech. Biochem.* 59:1095–1098 (1995)).

Non-plasmid containing microorganisms, while less efficacious than those described above, have also been used as threonine producers. Strains of *E. coli* such as H-8460, which is obtained by a series of conventional mutagenesis and selection for resistance to several metabolic analogs makes about 75 g/L of L-threonine in 70 hours (Kino et al., U.S. Pat. No. 5,474,918). Strain H-8460 does not carry a recombinant plasmid and has one copy of the threonine biosynthetic genes on the chromosome. The lower productivity of this strain compared to the plasmid-bearing strains, such as BKIIM B-3996, is believed to be due to lower enzymatic activities particularly those encoded by the thr operon) as these non-plasmid containing strains carry only a single copy of threonine biosynthetic genes. Other examples of suitable non-plasmid containing microorganisms are described, for example, in U.S. Pat. Nos. 5,376,538; 5,342,766; 5,264,353; 5,217,883; 5,188,949; 5,164,307; 5,098,835; 5,087,566; 5,077,207; 5,019,503; 5,017,483; 4,996,147; 4,463,094; 4,452,890; 3,732,144; 3,711,375; 3,684,654; 3,684,653; 3,647,628; 3,622,453; 3,582,471; 3,580,810; 3,984,830; and 3,375,173.

In both the non-plasmid and plasmid containing strains of *E. coli*, the thr operon is controlled by the particular strain's respective native threonine promoter. As described above, the expression of the native promoter is regulated by an attenuation mechanism controlled by a region of DNA which encodes a leader peptide and contains a number of threonine and isoleucine codons. This region is translated by a ribosome which senses the levels of threoninyl-tRNA and isoleucinyl-tRNA. When these levels are sufficient for the leader peptide to be translated, transcription is prematurely terminated, but when the levels are insufficient for the leader peptide to be translated, transcription is not terminated and the entire operon is transcribed, which, following translation, results in increased production of the threonine biosynthetic enzymes. Thus, when threonyl-tRNA and/or isoleucinyl-tRNA levels are low, the thr operon is maximally transcribed and the threonine biosynthetic enzymes are maximally made.

In the *E. coli* threonine-producing strain BKIIM B-3996, the threonine operon in the plasmid is controlled by its native promoter. As a result, the thr operon is only maximally expressed when the strain is starved for threonine and/or isoleucine. Since starvation for threonine is not possible in a threonine-producing strain, these strains have been rendered auxotrophic for isoleucine in order to obtain a higher level of enzymatic activity.

Another way of overcoming attenuation control is to lower the level(s) of threonyl-tRNA and/or isoleucinyl-tRNA in the cell. A thrs mutant, for example, having a threonyl-tRNA synthase which exhibits a 200-fold decreased apparent affinity for threonine, results in overexpression the thr operon, presumably due to the low level of threonyl-tRNA (E. J. Johnson et al., *J. Bacteriol.* 129:66–70 (1977)).

In fermentation processes using these strains, however, the cells must be supplemented with isoleucine in the growth stage because of their deficient isoleucine biosynthesis. Subsequently, in the production stage, the cells are deprived of isoleucine to induce expression of the threonine biosynthetic enzymes. A major drawback, therefore, of using native threonine promoters to control expression of the threonine biosynthetic enzymes is that the cells must be supplemented with isoleucine.

The antibiotic borrelidin is also known to reduce the enzymatic activity of threonyl tRNA-synthetase, and thereby inhibit the growth of *E. coli* (G. Nass et al., *Biochem. Biophys. Res. Commun.* 34:84 (1969)). In view of this reduced activity, certain borrelidin-sensitive strains of *E. coli* have been employed to produce high levels of threonine (Japanese Published Patent Application No. 6752/76; U.S. Pat. No. 5,264,353). Addition of borrelidin to the culture was found to increase the yield of L-threonine. Borrelidin-sensitive strains of Brevibacterium and Corynebacterium have also been used to produce high levels of threonine (Japanese Patent No. 53-101591).

Borrelidin-resistant mutants of *E. coli* similarly exhibit changes in threonyl tRNA-synthestase activity. More specifically, borrelidin-resistant *E. coli* have been shown to exhibit one of the following features: (i) constitutively increased levels of wild-type threonyl tRNA-synthetase; (ii) structurally altered threonyl tRNA-synthetase; or (iii) some unknown cellular alteration, probably due to a membrane change (G. Nass and J. Thomale, *FEBS Lett.* 39:182–186 (1974)). None of these mutant strains, however, has been used for the fermentative production of L-threonine.

In view of the discussion above, there remains a need in the art for microorganism strains which efficiently produce amino acids such as threonine, but without the problems associated with the state of the art.

SUMMARY OF THE INVENTION

It is therefore an object of the present invention to provide microorganisms which efficiently produce L-threonine in high yields, but which do not require any recombinant plasmids containing genes that encode threonine biosynthetic enzymes and preferably have no amino acid nutritional requirements. Other objects, features and advantages of the present invention will be set forth in the detailed description of preferred embodiments that follows, and in part will be apparent from the description or may be learned by practice of the invention. These objects and advantages of the invention will be realized and attained by the methods particularly pointed out in the written description and claims hereof These and other objects are accomplished by the methods of the present invention, which, in a first embodiment, is directed to a process for producing amino acids such as L-threonine, which comprises the steps of culturing a strain of *E. coli* in a medium and recovering the amino acid from the medium. The strain of *E. coli* used in this process has the following characteristics: (i) it contains a genetic determinant of amino acid biosynthesis, such as the threonine operon (which encodes the threonine biosynthetic enzymes), on the chromosome under control of a non-native promoter; and (ii) it does not require any recombinant plasmids containing genes that encode threonine biosynthetic enzymes to produce threonine.

Another embodiment of the present invention is directed to a biologically pure culture of a strain of *E. coli* having the above characteristics.

An additional embodiment of the present invention is directed to a process for producing amino acids such as L-threonine, which comprises the steps of culturing a strain of *E. coli* in a medium and recovering the amino acid from the medium, wherein the strain of *E. coli* is resistant to borrelidin.

A further embodiment of the present invention is directed to a method of producing a strain of *E. coli* useful for the fermentative production of amino acids such as threonine which comprises the steps of (a) introducing genetic material from an amino acid-producing microorganism into the chromosome of an *E. coli* auxotroph so as to render that *E. coli* prototrophic; (b) inserting a non-native promoter into the chromosome before the chromosomal location of the amino acid biosynthetic genes to control the expression thereof; and, optionally, (c) removing amino acid nutritional requirements for and/or regulatory hindrances to amino acid biosynthesis from the chromosome.

It is to be understood that both the foregoing general description and the following detained description are exemplary and explanatory only and are intended to provide further explanation of the invention as claimed.

DETAILED DESCRIPTION OF PREFERRED EMBODIMENTS OF THE INVENTION

Figure 1:
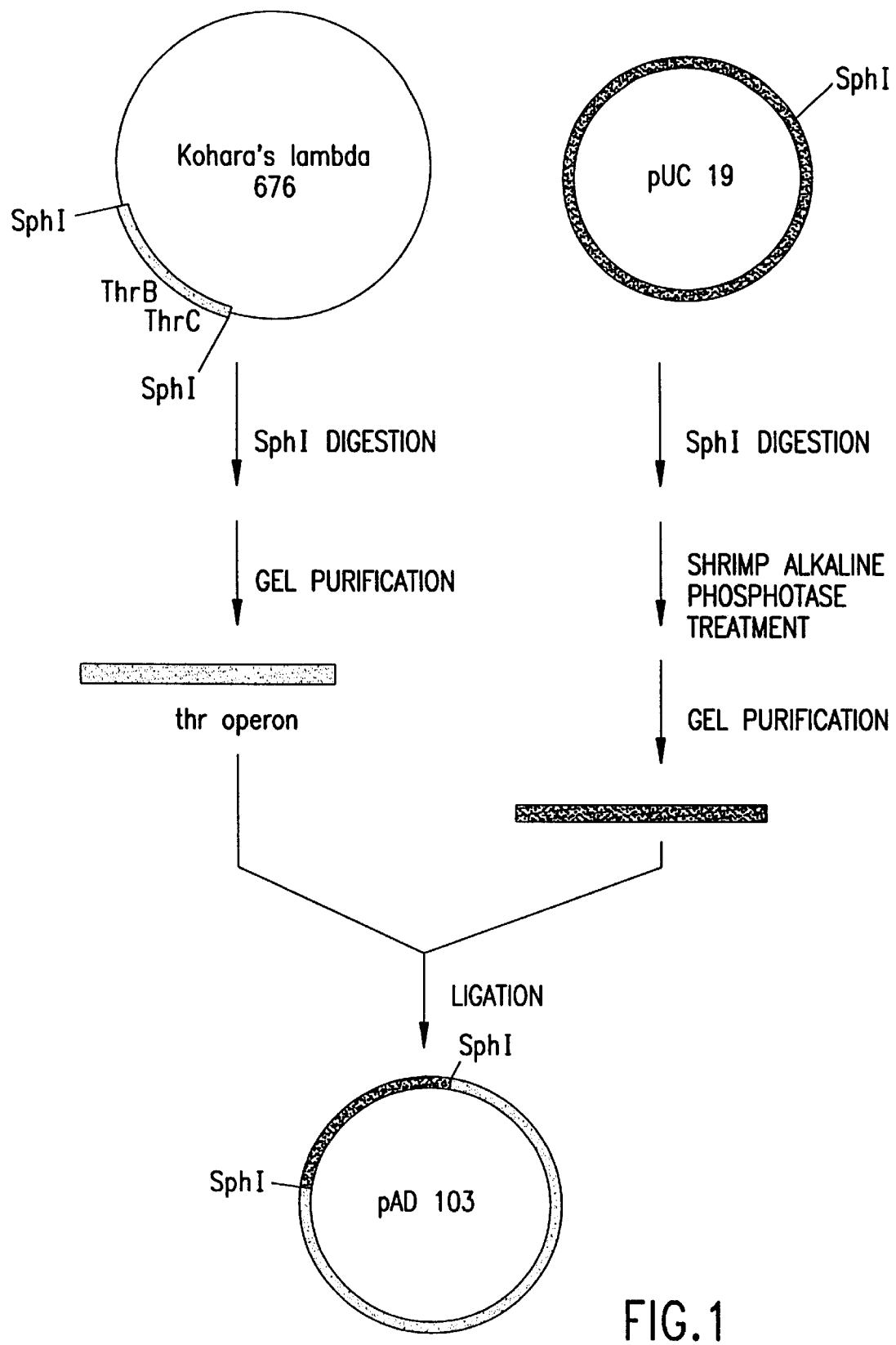
FIG. 1 depicts the construction of plasmid pAD103 from Kohara's lambda 676 and plasmid pUC19.
Figure 2:
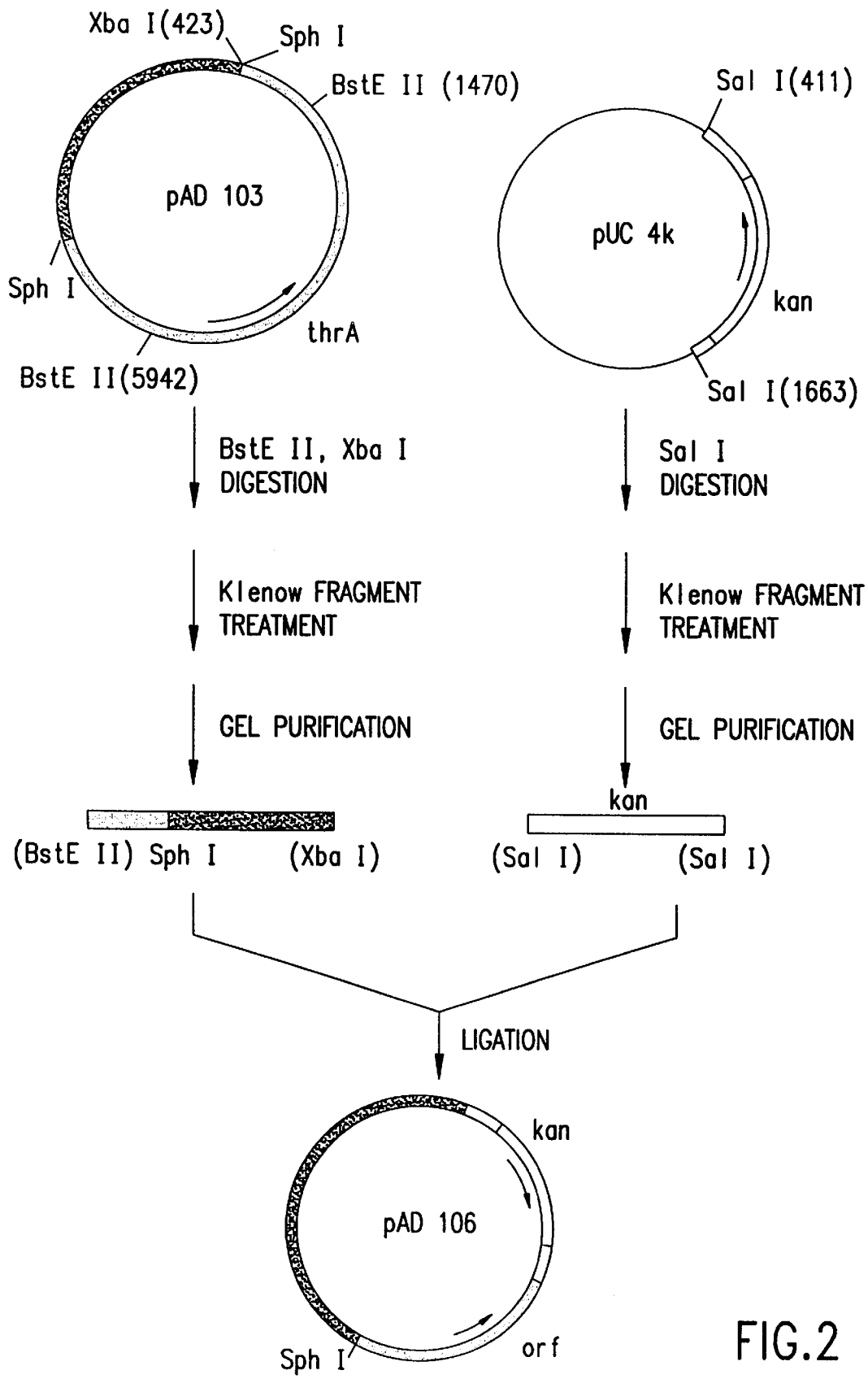
FIG. 2 depicts the construction of plasmid pAD106 from plasmid pAD103 and plasmid pUC4k.
Figure 3:
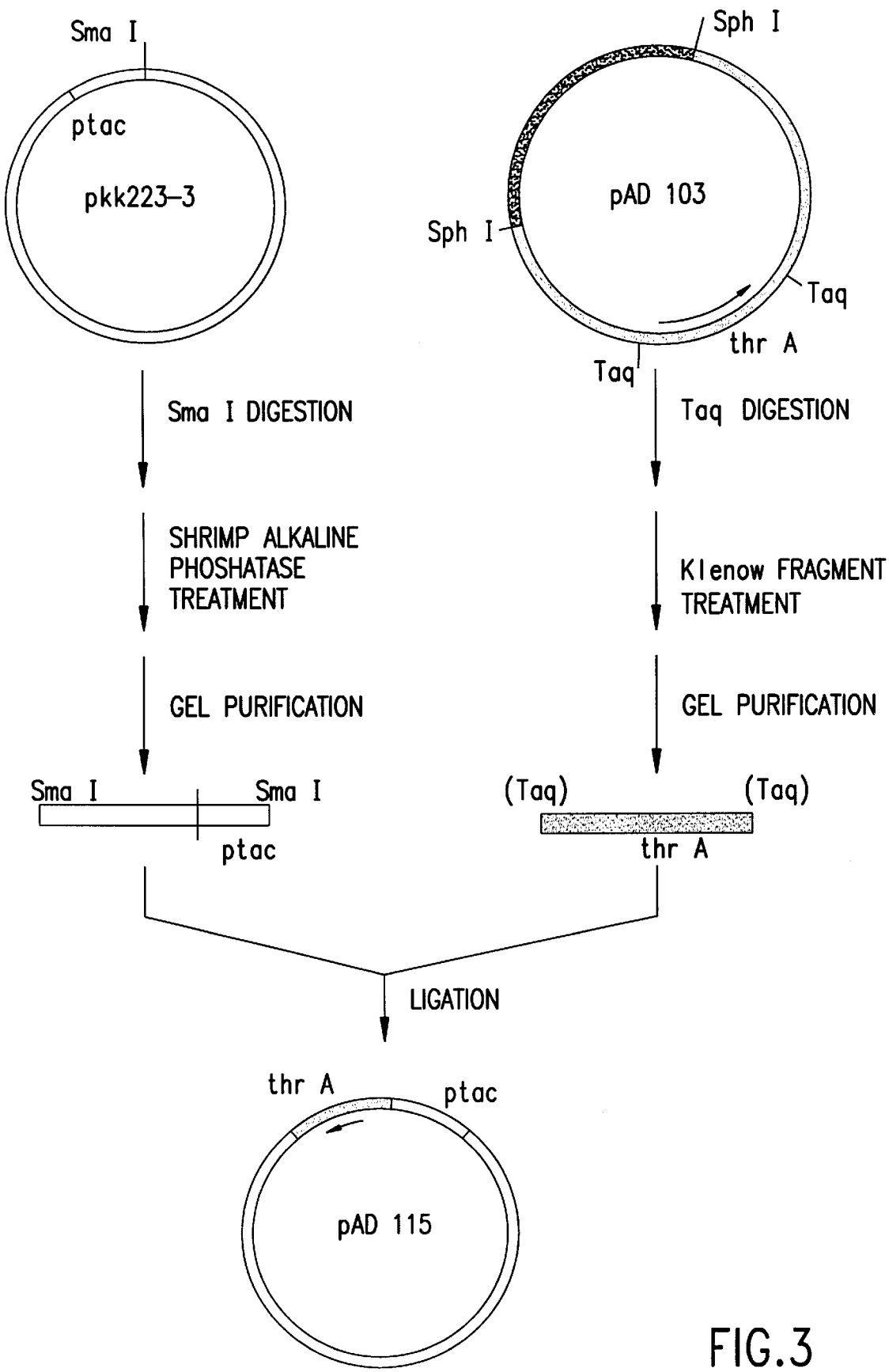
FIG. 3 depicts the construction of plasmid pAD115 from plasmid pAD103 and plasmid pkk223-3.
Figure 4:
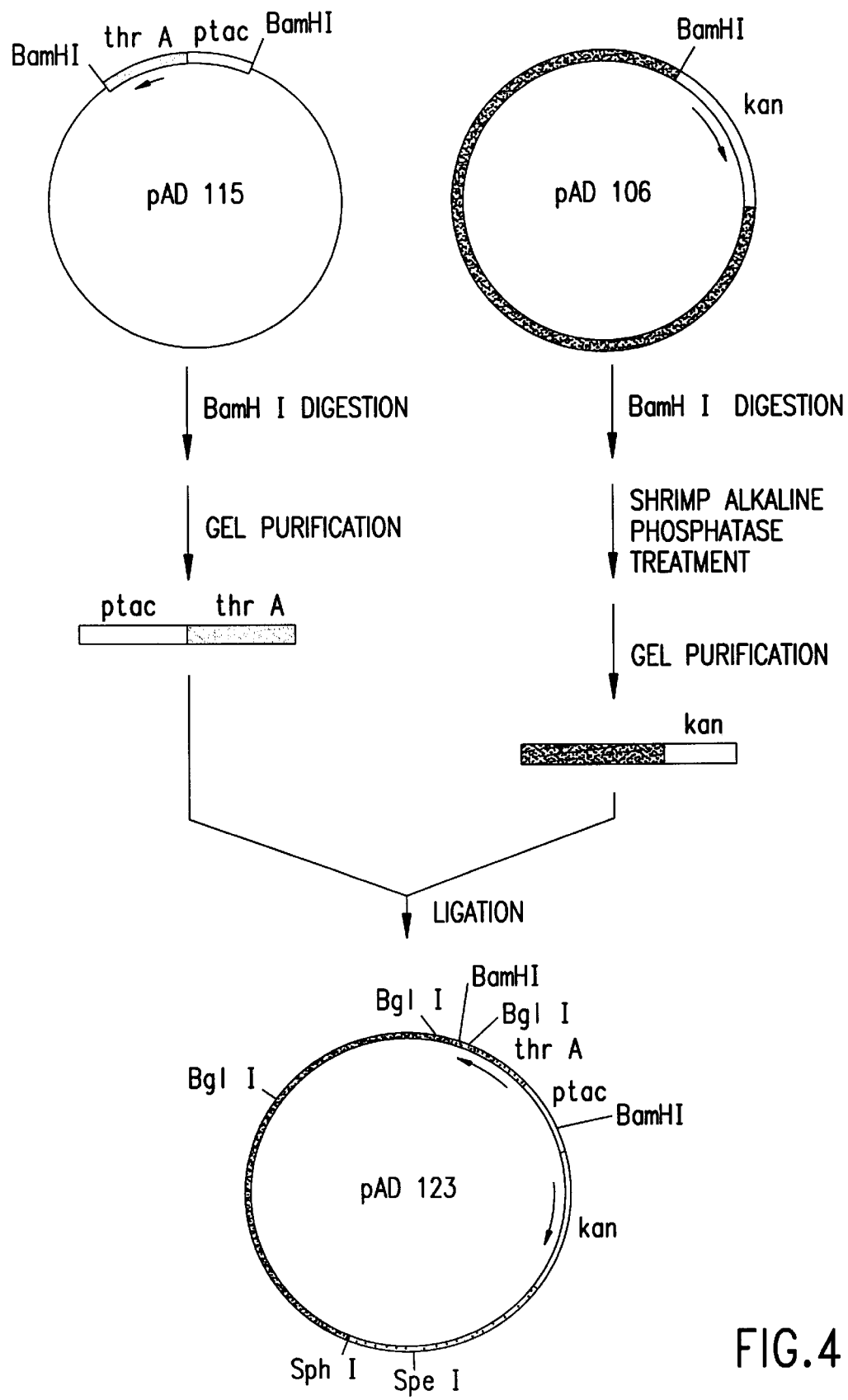
FIG. 4 depicts the construction of plasmid pAD123 from plasmid pAD115 and plasmid pAD106.
Figure 5:
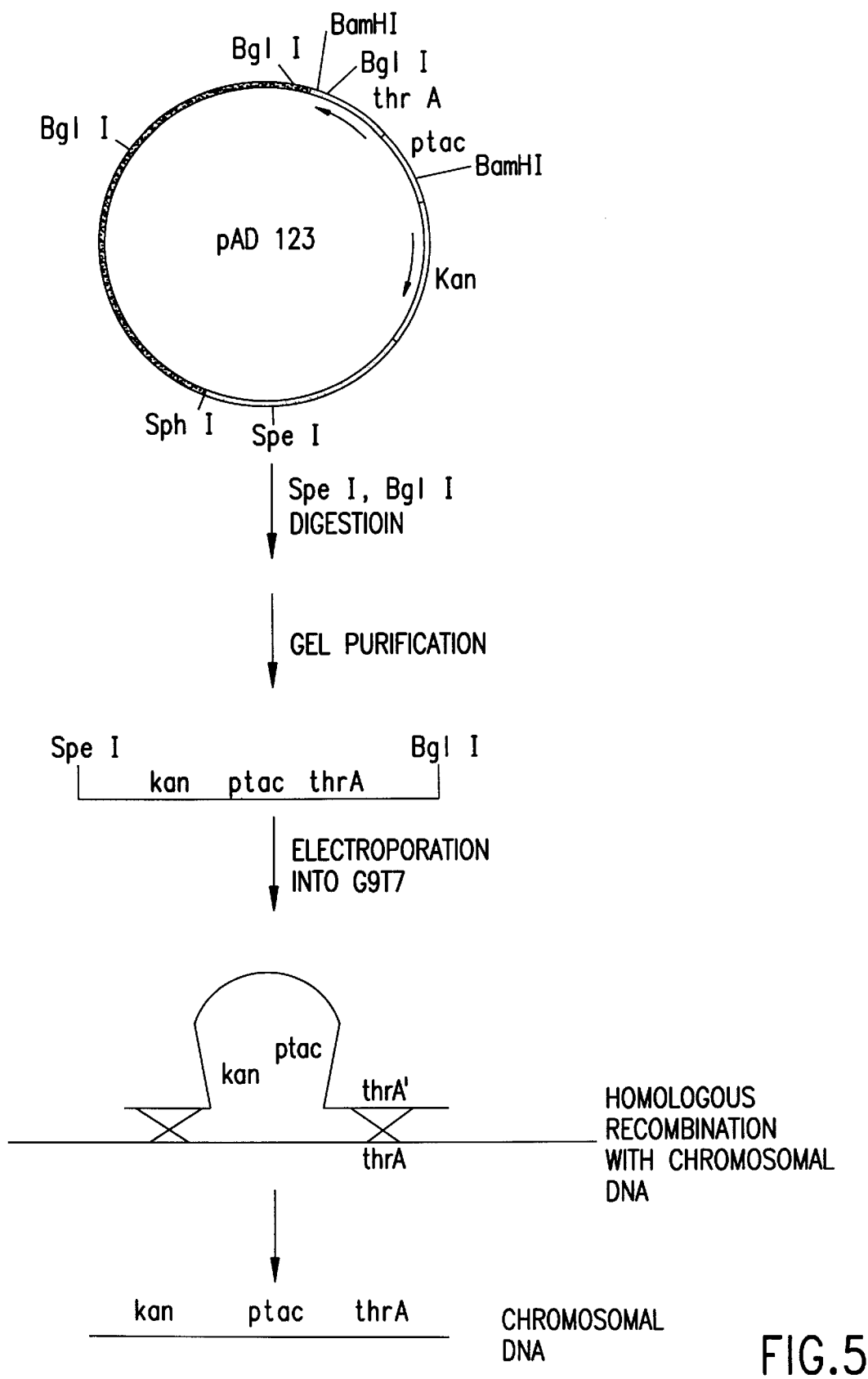
FIG. 5 depicts the intergration of the promoter region from plasmid pAD123 into the chromosome of *E. coli*.

In a first embodiment, the present invention is directed to novel bacterial strains which may be used in fermentation processes for the production of amino acids. The novel bacterial strains of the present invention have the following characteristics:

(i) the cells contain at least one thr operon, i.e., at least one set of the genes encoding the threonine biosynthetic enzymes, on the chromosome under the control of a non-native promoter; and (ii) the cells do not require any recombinant plasmids encoding the threonine biosynthetic enzymes in order to produce threonine.

Preferably, the inventive strains are capable of producing at least about 50 g/L of L-threonine in about 30 hours, more preferably at least about 70 g/L in about 30 hours, even more preferably at least about 80 g/L in about 30 hours, and most preferably about at least about 90 g/L in about 30 hours. Preferably, the inventive strains are capable of producing at least about 90 g/L in about 48 hours, more preferably at least about 100 g/L in about 48 hours, and most preferably at least about 110 g/L of threonine in about 48 hours.

Preferably, the inventive strains are capable of producing L-threonine at a rate of at least about 2 g/L/hr, more preferably at least about 2.5 g/L/hr, even more preferably at least about 3 g/L/hr, and most preferably at least about 3.6 g/L/hr.

In a particularly preferred embodiment, the novel bacterial strains also have no amino acid nutritional requirements for fermentative production of threonine, i.e., the cells do not require amino acids supplements for growth and threonine production.

According to the present invention, the inventive bacterial strain does not require any recombinant plasmids containing one or more genes that encode threonine biosynthetic enzymes for threonine production, i.e., the strain is capable of producing threonine without the need for one or more of the threonine biosynthetic enzymes to be encoded by genes contained in a recombinant plasmid. The inventive strains may, of course, optionally contain one or more recombinant plasmids as desired. For example, while such plasmids are not required for threonine production, the inventive strains may nevertheless contain recombinant plasmids that encode for threonine biosynthetic enzymes in order to increase threonine production. The inventive strains may likewise contain recombinant plasmids encoding other enzymes involved in threonine biosynthesis, such as aspartate semialdehyde dehydrogenase (asd).

Preferably, the inventive bacterial strains are strains of *Escherichia coli*. More preferably, the inventive bacterial strains are strains of *E. coli* that exhibit resistance to the macrolide anitbiotic borrelidin. A particularly preferred example of the inventive bacterial strains is *E. coli* strain kat-13, which was deposited at the Agricultural Research Service Culture Collection (NRRL), 1815 North University Street, Peoria, Ill. 61604, USA, on Jun. 28, 1996 and assigned accession number NRRL B-21593.

The threonine (thr) operon on the chromosome of the cells of the inventive bacterial strains encodes the enzymes necessary for threonine biosynthesis. Preferably, the threonine operon consists of an AK-HD gene (thrA or metL), a homoserine kinase gene (thrB), and a threonine synthase gene (thrC). More preferably, the thr operon consists of thrA (the AK I-HD I gene), thrB and thrC. Suitable thr operons may be obtained, for example, from *E. coli* strain ATCC 21277 and strain ATCC 21530. The thr operon from strain ATCC 21277 is particularly preferred. Multiple copies of the thr operon may be present on the chromosome.

Preferably, the thr operon contains at least one non-attenuated gene, i.e., expression of the gene is not suppressed by the levels (extra- and/or intracellular) of one or more of the threonine biosynthetic enzymes and/or the products thereof (e.g. threonine and isoleucine). The inventive strain may also contain a thr operon that contains a defective thr attenuator (the regulatory region downstream of the transcription intitation site and upstream of the first structural gene) or a thr operon that lacks the thr attenuator altogether.

In a particularly preferred embodiment of the present invention, the thr operon encodes one or more feedback-resistant threonine biosynthetic enzymes, i.e., the activity of the enzyme is not inhibited by the extra- and/or intracellular levels of the intermediates and products of threonine biosynthesis. Most preferably, the thr operon contains a gene that encodes a feedback-resistant AK-HD, such as a feedback-resistant AK I-HD I. Use of a feedback-resistant AK-HD provides a higher level of enzymatic activity for threonine biosynthesis, even in the presence of the L-threonine being produced.

Expression of the threonine operon(s) in the inventive strains is controlled by a non-native promoter, i.e., a promoter that does not control the expression of the thr operon in *E. coli* bacterial strains normally found in nature. Replacing the native promoter of the threonine biosynthetic enzymes with a strong non-native promoter to control the expression of the thr operon results in higher threonine production even with only a single, genomic copy of the thr operon. In addition, since a non-native promoter is used to control the expression of threonine operon, it is not necessary to render the bacterial strains auxotrophic for isoleucine to achieve this higher threonine production. Illustrative examples of suitable promoters include, but are not limited to: the lac promoter; the trp promoter; the $P_L$ promoter of λ bacteriophage; the $P_R$ promoter; the lpp promoter; and the tac promoter. Particularly preferred for use in the inventive bacterial strains is the tac promoter.

In addition to the threonine operon, the chromosome in the cells of the inventive bacterial strains preferably also contains at least one gene encoding aspartate semialdehyde dehydrogenase (asa). Most preferably, the chromosome in the cells of the present invention contains at least one asd gene, at least one thrA gene, at least one thrB gene and at least one thrC gene. The chromosome may, of course, contain multiple copies of one or more of these genes.

Threonine dehydrogenase (tdh) catalyzes the oxidation of L-threonine to α-amino-β-ketobutyrate. Accordingly, in an especially preferred embodiment, the chromosome of the inventive cells further contains at least one defective threonine dehydrogenase (tdh⁻) gene. The defective tdh gene may be a gene having a reduced level of expression of threonine dehydrogenase or a gene that encodes a threonine dehydrogenase mutant having reduced enzymatic activity relative to that of native threonine dehydrogenase. Preferably, the defective tdh gene employed in the inventive strain does not express threonine dehydrogenase. Illustrative examples of suitable tdh genes that do not express threonine dehydrogenase include a tdh gene having a chloramphenicol acetyltransferase (cat) gene inserted into it or a tdh gene having transposon Tn5 inserted into it, as described in U.S. Pat. No. 5,175,107.

The bacterial strains of the present invention may be prepared by any of the methods and techniques known and available to those skilled in the art. Illustrative examples of suitable methods for constructing the inventive bacterial strains include mutagenesis using suitable agents such as NTG; gene integration techniques, mediated by transforming linear DNA fragments and homologous recombination; and transduction mediated by the bacteriophage P1. These methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989).

In a particularly preferred embodiment of the invention, *E. coli* strain 472T23, which requires threonine for growth, may be converted to a threonine producer using P1-mediated transduction to introduce the threonine operon of *E. coli* strain ATCC 21277, which may be obtained from the American Type Culture Collection, 12301 Parklawn Drive, Rockville, Md. 20852, USA. This thr operon consists of a feedback resistant aspartate kinase-homoserine dehydrogenase gene (thrA), a homoserine kinase gene (thrB), and a threonine synthase gene (thrC).

To improve threonine production in the inventive strains, the defective threonine dehydrogenase gene from *E. coli* strain CGSC6945 (relevant genotype: tdh-1::cat1212; obtained from the *E. coli* Genetic Stock Center, 355 Osborne Memorial Laboratory, Department of Biology, Yale University, New Haven, Conn. 06520-8104, USA) may be introduced by P1 transduction. The resulting threonine producer may be further improved by mutagenizing with NTG and/or selecting for borrelidin resistance.

Plasmids carrying an antibiotic resistance marker gene, such as kan (which encodes for kanomycin resistance), and a strong promoter, such as $P_L$ or tac, preferably flanked by DNA upstream of thrA and a few hundred base pairs of the wild-type thrA gene (i.e., not the whole thrA gene), may be constructed and used as a vehicle to deliver the desired DNA fragments into the chromosome. The fragment on the plasmid may be isolated by digestion with a suitable restriction enzyme and purified, and then introduced, through transformation or electroporation, into a strain to remove the control region of threonine operon and replace it by homologous recombination with the desired fragment, i.e., an antibiotic resistance marker gene and a strong promoter at the beginning the thrA gene. This fragment may then be transferred into the borrelidin resistant strain by P1 transduction.

The isoleucine requirement of the strain of the preferred host, 472T23, may be eliminated, for example, by introducing a wild type allele of the marker through P1 transduction. Unwanted nutritional requirements of other hosts may be removed in a similar manner or according to other methods known and available to those skilled in the art.

A second embodiment of the present invention is directed to the use of the above-described bacterial strains in fermentation processes for the production of amino acids of the aspartate family. L-threonine, for example, is obtained by culturing the inventive bacterial strains in a synthetic or natural medium containing at least one carbon source, at least one nitrogen source and, as appropriate, inorganic salts, growth factors and the like.

Illustrative examples of suitable carbon sources include, but are not limited to: carbohydrates, such as glucose, fructose, sucrose, starch hydrolysate, cellulose hydrolysate and molasses; organic acids, such as acetic acid, propionic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing, including meat extract, peptone, corn steep liquor, casein hydrolysate, soybean cake hydrolysate and yeast extract.

After cultivation, the L-threonine that has accumulated in the culture broth can be separated according to any of the known methods, e.g., by use of ion-exchange resins as described in U.S. Pat. No. 5,342,766. This method involves first removing the microorganisms from the culture broth by centrifugation and then adjusting the pH of the broth to about 2 using hydrochloric acid. The acidified solution is subsequently passed through a strongly acidic cation exchange resin and the adsorbent eluted using dilute aqueous ammonia. The ammonia is removed by evaporation under vacuum, and the resulting solution is condensed. Addition of alcohol and subsequent cooling provides crystals of L-threonine.

Other amino acids of the aspartate family can be produced by methods similar to that described in detail above. Isoleucine, for example, can be prepared from the inventive bacterial strains containing, on the chromosome or on a plasmid, an amplified ilvA gene or tdc gene, both of which encode threonine deaminase, the first enzyme involved in the bioconversion of threonine to isoleucine. Amplification of this gene, for example, by use of a ilvA gene encoding a feedback-resistant enzyme, leads to increased biosynthesis of isoleucine.

Similarly, methionine can be prepared by microorganisms such as E. coli that contain at least one met operon on the chromosome, i.e. the metL gene (which encodes AK II-HD II), the metA gene (homoserine succinyltransferase), the metB gene (cystathionine γ-synthase), the metC gene (cystathionine P-lyase) and the metE and metH genes (homocysteine methylase). These genes, including feedback-resistant variants thereof, and, optionally, a non-native promoter can be introduced into the chromosome of the host microorganism according to one or more of the general methods discussed above and/or known to those skilled in the art. Lysine can likewise be prepared by microorganisms that contain a gene encoding the lysine biosynthetic enzymes (preferably a feedback-resistant lysine biosynthetic enzyme encoded by lysC and/or dapa) and, optionally, a non-native promoter.

A third embodiment of the present invention is directed to the use of borrelidin-resistant bacterial strains in fermentation processes for the production of L-threonine. Preferably, the borrelidin-resistant strains are mutants of an E. coli strain. A particularly preferred embodiment of such a mutant is E. coli strain kat-13, which was deposited at the Agricultural Research Service Culture Collection (NRRL), 1815 North University Street, Peoria, Ill. 61604, USA, on Jun. 28, 1996 and assigned accession number NRRL B-21593.

Borrelidin resistance may be determined by any of the accepted methods known to those skilled in the art. For example, borrelidin-resistant strains can be isolated by plating the candidate strains on minimal medium containing about 139 μM borrelidin, as described in G. Nass and J. Thomale, *FEBS Lett.* 39:182–186 (1974). In addition, borrelidin resistance in certain strains is manifested as a change in one or more phenotypic characteristics of the cells. For example, borrelidin-resistant mutants of E. coli strain 6–8 and its derivatives appear round, rather than as rods. In such cases, evidence of a change in a phenotypic characteristic may be sufficient to adequately identify borrelidin-resistant strains.

The borrelidin-resistant mutants useful in this embodiment of the present invention are capable of producing threonine. The genes that encode the threonine biosynthetic enzymes may be present on the chromosome or contained in plasmids or mixtures thereof. Multiple copies of these genes may also be present. Preferably, the genes that encode the threonine biosynthetic enzymes are resistant to attenuation control and/or encode feedback-resistant enzymes.

As noted above, the inventive borrelidin-resistant strains may contain one or more recombinant plasmids as desired. For example, the inventive microorganisms may contain recombinant plasmids that encode for threonine biosynthetic enzymes. The inventive bacterial strains may likewise contain recombinant plasmids encoding other enzymes involved in threonine biosynthesis, such as aspartate semialdehyde dehydrogenase (asd), or enzymes to augment growth.

Additionally, the borrelidin-resistant strains may be modified as desired, for example, in order to increase threonine production, remove nutritional requirements, and the like, using any of the methods and techniques known and available to those skilled in the art. Illustrative examples of suitable methods for modifying borrelidin-resistant E. coli mutants and variants include, but are not limited to: mutagenesis by irradiatiton with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by transforming linear DNA fragments and homologous recombination; and transduction mediated by bacteriophages such as P1. These methods are well known in the art and are described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, N.Y. (1989).

Preferably, the borrelidin-resistant mutants of the present invention are modified so as to include a non-native promoter upstream of and in operable link with one or more of the genes that encode the threonine biosynthetic enzymes, regardless of whether these genes are on the chromosome and/or contained in plasmids.

According to a particularly preferred mode of this embodiment of the present invention, L-threonine is obtained by culturing at least one borrelidin-resistant bacterial strain in a synthetic or natural medium containing at least one carbon source, at least one nitrogen source and, as appropriate, inorganic salts, growth factors and the like, as described above. Accumulated threonine can be recovered by any of the methods known to those skilled in the art.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLE 1

Preparation of E. coli strain kat-13

A. Transfer of the threonine operon of *E. coli* strain ATCC 21277 into the chromosome of *E. coli* strain 472T23.

*E. coli* strain ATCC 21277 (U.S. Pat. No. 3,580,810), available from the American Type Culture Collection, 12301 Parklawn Drive, Rockville, Md. 20852, USA, is amino-β-hydroxyvaleric acid (AHV) resistant but requires proline, thiamine, isoleucine, methionine to grow in a minimal medium. ATCC 21277 is reported to accumulate 6.20 g/L of threonine in a fermentation process. The threonine operon of ATCC 21277 consists of an aspartate kinase 1-homoserine dehydrogenase I gene (thrA) that encodes a feedback-resistant enzyme, a homoserine kinase gene (thrB), and a threonine synthase gene (thrC).

*E. coli* strain 472T23, which is deposited in the USSR Collection of Commercial Microorganisms at USSR Antibiotics Research Institute under Reg. No. BKIIM B-2307, is reported to require threonine and isoleucine to grow in a minimal medium which contains glucose, ammonia, vitamin B1, and mineral salts. This strain cannot produce threonine because it carries a defective thrC gene, an essential gene for threonine biosynthesis. The strain 472T23 also carries a defective threonine deaminase gene, ilvA, which codes for the first enzyme in isoleucine biosynthesis.

Bacteriophage P1 lysate was prepared by growing phage on ATCC 21277. Strain 472T23 was then infected with this P1 lysate, in which a small number of the phage particles carried the threonine operon of ATCC 21277. Following infection, bacteria synthesizing threonine were selected by spreading on minimal medium E [glucose 0.05 g/L; $MgSO_4 \cdot 7H_2O$ 0.2 g/L; citric acid $H_2O$ 2.0 g/L; $K_2HPO_4$ 10.0 g/L; $NaHN_4PO_4 \cdot 4H_2O$ 3.5 g/L; agar 15.0 g/L] agar plates supplemented with 0.25 g/L isoleucine. Several threonine prototrophic transductants, which carried the threonine operon of ATCC 21277, were now able to grow in a minimal plates supplemented only with isoleucine.

These transductants were screened by shake-flask fermentation for threonine production as described below in Example 2. One of them, G9, producing threonine, was selected for further strain development.

B. Transfer of a defective threonine dehydrogenase (tdh⁻) gene inserted with a chloramphenicol acetyltransferase (cat) gene into the chromosome of *E. coli* strain G9.

Strain CGSC6945, carrying a defective threonine dehydrogenase gene (tdh⁻), was obtained from the *E. coli* Genetic Stock Center, 355 Osborne Memorial Laboratory, Department of Biology, Yale University, New Haven, Conn. 06520-8104, USA. The threonine dehydrogenase gene is defective because inserted into it is the chloramphenicol acetyltransferase (cat) gene. To transfer this defective gene to G9, P1 phage were grown on CSCG6945, and the lysate was used to infect G9. Several chloramphenicol-resistant transductants of G9 were selected and screened for threonine production with shake-flask fermentation as described below in Example 2. One of them, G909, with a higher threonine titer than G9, was selected for further development.

C. Insertion of a non-native promoter into the chromosome of *E. coli* strain G909.

In order to deliver the tac promoter into the chromosome of G909, homologous recombination between a linear DNA fragment and the chromosome of an exonuclease V minus strain (recD) was employed.

The linear DNA fragment contained 1.5 kb of the sequence upstream (5' end) of the threonine operon, a kanamycin resistant marker, the tac promoter sequence, and about 480 bp of the thrA gene. This fragment, which provided 5' end homology, a selection marker (kanamycin resistance), a strong and controllable promoter to the threonine operon (tac), and 3'end homology, respectively, was generated as follows.

The threonine operon of the wild type *E. coli* W3110 was cloned into the restriction enzyme SphI site of plasmid pUC19 by using the DNA of the lambda clone 676 from Dr. Yuji Kohara, Department of Molecular Biology, School of Science, Nagoya University, Chikusa-ku, Nagoya, Japan. The DNAs of lambda clone 676 and pUC19 were then digested with SphI. The pUC19 fragment was subsequently dephosphorylated with shrimp alkaline phosphatase (SAP) and agarose-gel purified. The 6.9 kb fragment of threonine operon from lambda clone was also purified. These two fragments were subsequently ligated by T4 DNA ligase to generate plasmid pAD103.

An upstream flanking region for homologous recombination and kanamycin resistance marker was then constructed. pAD103 was digested with restriction enzyme BstEII, XbaI and blunt-ended with klenow fragment treatment. The 1.5 kb fragment containing only the 5'end (upstream) of the threonine operon (but not the thr operon itself or its control region) was isolated and ligated to the fragment of kanamycin resistance gene from pUC4K (Pharmacia), which was digested with restriction enzyme SalI and klenow fragment treated to fill-in the 3' overhangs to generate intermediate plasmid pAD106.

pAD103 was also digested with restriction enzyme TaqI and blunt-ended with klenow fragment treatment. The fragment containing the native ribosome binding site and about 480 bp of the coding sequence of the thrA gene was isolated and then ligated to a fragment of pKK233-3 (Pharmacia), which had been digested with restriction enzyme SmaI and dephosphorylated with SAP, to obtain plasmid pAD115, which contained the DNA sequence of the tac promoter, the ribosome binding sites and a few hundred bases of the thrA gene.

pAD115 was subsequently digested with restriction enzyme BamHI and 0.75 kb of the DNA fragment which contained the desired DNA sequences was isolated. pAD106 was also digested with BamHI and then dephosphorylated with SAP. The two fragments were then ligated to provide plasmid pAD123, which contained the DNA sequence upstream of the threonine operon, a kanamycin resistance marker gene, the tac promoter, and about 480 bp of the beginning of the thrA gene.

pAD123 was then digested with SpeI, BglI and the fragment containing the desired DNA sequences was isolated.

The exonuclease V minus strain (recD) was prepared by growing P1 phage on *E. coli* strain KW251 (relevant genotype: argA81::Tn10, recD1014; obtained from Pharmacia), which contains a recD gene with a cotransducible transposon Tn10 insertion in argA. The lysate which was prepared from the phage was then used to infect strain G9 and the tetracycline-resistant transductant G9T7 was isolated.

The DNA fragment from plasmid pAD123 was delivered to E. coli strain G9T7 by electroporation. A kanamycin-resistant strain of G9T7 was isolated and a P1 phage lysate was made by growing phage on this strain. The P1 phage lysate was then used to transduce G909. One of the kanamycin-resistant transductants of G909, tac3, which showed a higher threonine titer in the presence of IPTG in shake-flask study, was isolated.

P1 phage lysate was subsequently prepared with strain tac3 and then used to infect strain 6–8 (described below). The kanamycin-resistant transductants were selected and one of them, strain 6–8tac3, which produced a even higher titer than tac3 in a shake-flask study, was isolated.

D. NTG mutagenesis and the isolation of borrelidin-resistant mutants from E. coli strains G909 and 6–8.

The cells of strain G909 were mutagenized by N-methyl-N'-nitro-N-nitrosoguanidine (NTG) treatment (50 mg/L, 30 min. at 36° C.) using conventional methods. The resulting cells were then spread on minimal medium E agar plate containing 0.25 g/L of L-isoleucine and 0.1% v/v of borrelidin. After incubation for 3–5 days at 36° C., the large colonies that formed on the plate, which included strain 6–8, were selected for testing for borrelidin resistance and L-threonine production.

To test for borrelidin resistance, each strain was cultivated in 20 ml of the seed medium SM [32.5 g/L glucose; 1 g/L $MgSO_4.7H_2O$; 24.36 g/L $K_2HPO_4$; 9.52 g/L $KH_2PO_4$; 5 g/L $(NH_4)_2SO_4$; 15 g/L yeast extract; pH 7.2] at 36° C. for 17 hr with shaking. The cells were harvested and washed with minimal medium E. The cell suspension was then inoculated into a sterilized tube containing 3 ml of minimal medium E and 0, 0.1, 0.5, or 1 mM borrelidin. After 24 hr cultivation at 36° C. with shaking, growth was determined by measuring the optical density at 660 nm. The results are shown below relative to growth in the absence of borrelidin.

| borrelidin (mM) | G909 | 6-8 |
| --- | --- | --- |
| 0 | 100.0 | 100.0 |
| 0.1 | 24.2 | 134.5 |
| 0.5 | 2.9 | 141.0 |
| 1 | 0.9 | 184.5 |

E. Removal of isoleucine requirement and lactose repressor gene (lacI).

By introducing the non-native tac promoter and a feedback-resistant thrA gene, expression of the thr operon (thrA, thrB, thrC) is no longer controlled by the attenuation mechanism. As a result, starvation for isoleucine and/or the presence of an ilvA⁻ auxotrophic marker is no longer required for threonine production.

Accordingly, the wild type ilvA marker was introduced by transduction into 6–8tac3 to fix the isoleucine requirement of the strain, i.e., to eliminate the need for isoleucine-supplemented medium for cell growth. P1 phage lysate made from CGSC7334 (relevant genotype: lacI42::Tn10, lacZU118; obtained from the E. coli Genetic Stock Center, 355 Osborne Memorial Laboratory, Department of Biology, Yale University, New Haven, Conn. 06520-8104, USA) was used to infect 6–8tac3 and transductants positive for isoleucine biosynthesis were selected. These transductants produced approximately the same amount of L-threonine as strain 6–8tac3 in a shake-flask study. One of these transductants, 6–8tac3ile+ was selected for further development.

Since the threonine operon of 6–8tac3ile is under the control of the tac promoter, isopropyl-β-D-thiogalactoside (IPTG) was necessary to induce the cells to fully express the thr operon. The use of IPTG to induce expression of the thr operon, however, is less preferred according to the methods of the present invention.

Accordingly, to eliminate this unnecessary regulatory hindrance, a defective lac repressor (lacI) gene is introduced by infecting 6–8tac3ile+ with P1 phage made from CGSC7334. The resultant transductants (6–8tac3lacI−) were tested for resistance to tetracycline and tetracycline-resistant colonies were selected.

EXAMPLE 2

Shake-flask Fermentation Study of Threonine Production

A comparison of threonine production among the various E. coli strains was determined by their performance in shake-flask fermentation. The strains being tested were grown on LB agar medium [10 g/L of trypton, 5 g/L of extract, 15 g/L agar]. After 1 to 2 days of growth, the cells were suspended in 5 ml of seed medium [dextrose 32.5 g/L; $K_2HPO_4$ 24.35 g/L; $KH_2PO_4$ 9.5 g/L; yeast extract 15 g/L; $(NH_4)_2SO_4$ 5 g/L; $MgSO_4.7H_2O$ 1 g/L] at pH 7.2. The seed was grown for 24 hours with a stirring speed of 250 rpm at 37° C. 15 ml of fermentation medium [dextrose 40 g/L; yeast extract 2 g/L; citric acid 2 g/L; $(NH_4)_2SO_4$ 25 g/L; $MgSO_4.7H_2O$ 2.8 g/L; $CaCO_3$ 20 g/L; trace metal solution 2 mL] at pH 7.2 was then added to the seed and the fermentation process performed at 37° C. with a stirring speed of 250 rpm. After cultivation, the amount of L-threonine that had accumulated in the culture broth was analyzed by HPLC (ISCO Model 2353 pump, Rainin Model RI-1 refractive index detector, and aminex Hp87-CA column).

The amount of L-threonine produced by each of the tested strains is presented below.

| Strain | L-threonine produced (g/L) |
| --- | --- |
| G909 | 4.95 |
| 6-8 | 11.45 |
| tac3 | 12.9 (induced by IPTG) |
| | 10.6 (non-induced) |
| 6-8 tac3 ile+ | 12.7 (induced by IPTG) |
| 6-8 tac3 lacI− | 13.9 |
| kat 13 | 14.0 |

EXAMPLE 3

Fermentation Study

The E. coli strains of the present invention and their precursor strains were tested for L-threonine production by fermentation.

G909 was tested under the following conditions. 0.5 L of aqueous culture medium containing 30 g/L of tryptic soy broth and 5 g/L of yeast extract in a 2 L baffled shake flask was inoculated with 1.5 mL of G909 and incubated on shaker at 35° C. and 200 rpm for 8.5 hours. 0.9 mL (0.03%) of the mature inoculum was added to a glass fermentor containing 3.0 L of the seed fermentor medium [10 g/L d.s.

of corn steep liquor, 0.4 g/L of L-isoleucine, 2.5 g/L of KH$_2$PO$_4$, 2.0 g/L of MgS$_4$O .7H2O, 0.5 g/L of (,N$_2$H)$_4$SO, 0.192 g/L of anhydrous citric acid, 0.03 g/L of FeSO$_4$.7H$_2$O, 0.021 g/L of MnSO$_4$.H$_2$O and 80 g/L of dextrose]. Incubation was conducted under the following conditions: a temperature of 39° C. for the first 18 hours, and then 37° C. for the duration; pH of 6.9 (maintained by addition of NH$_4$OH); air flow of 3.5 LPM; agitation of 500 rpm initially, which was then increased to maintain the DO at 20%; and back pressure of 1–2 psi. Completion of the seed fermentor stage was determined by depletion of dextrose. 315 mL (15%) of the mature inoculum from the seed fermentor was added to a glass fermentor containing the same medium (main fermentor medium) listed above with the following exceptions: volume was 2.1 L and 0.34 g/L of L-isoleucine was added. Incubation was conducted for 48 hours under the following conditions: temperature of 37° C.; pH of 6.9 (maintained with NH$_4$OH); air flow of 3.5 LPM until 20 hours then increased to 4.0 LPM; agitation of 500 rpm initially, which was then increased to maintain the DO at 20%; back pressure of 1–2 psi; and dextrose level of 10 g/L (maintained by feeding with a 50% w/w dextrose solution). The fermentation was terminated after 48 hours. G909 produced the following results: a final titer of 62.3 g/L of threonine with a total productivity of 274 g and a yield of 23.2%.

tac3 was tested under the same conditions as G909 described above with the following exception: 1 mg/L of IPTG was added at the start of the main fermentor stage. With addition of IPTG, tac3 produced a final titer of 85.7 g/L of threonine with a total productivity of 355 g and a yield of 28.8%.

6–8 was tested under the same conditions as G909 described above. 6–8 produced the following results: a final titer of 74.1 g/L threonine with a total productivity of 290 g and a yield of 28.3%.

6–8tac3 was tested under the same conditions as tac3 described above, including the addition of IPTG. 6–8tac3 produced the following results: a final titer of 99.3 g/L threonine with a total productivity of 421 g and a yield of 35.1%.

6–8tac3ile+ was tested under the same conditions as 6–8tac3 as described above, with the following exception: no L-isoleucine was required in either the seed fermentor stage or the main fermentor stage. Due to an agitation failure at 22.5 hours, only the titer at 22 hours was recorded (62 g/L threonine).

kat-13 was tested under the same conditions as 6–8tac3 as described above with the following exception: no IPTG was added. Under these conditions, kat-13 produced a final titer of 102 g/L threonine with a total productivity of 445 g and a yield of 33.1%.

The relevant genotypes of the constructed strains, supplements required for fermentative production of threonine, and the titers recorded are presented in the Table below:

| Strain | Relevant Genotype | Supplements for production | titer at 30 hours | titer at 48 hours | Yield |
|---|---|---|---|---|---|
| G9 | ilvA⁻, | Ile | ND | ND | ND |
| G909 | ilvA⁻, tdh::Cm | Ile | 53 | 62.3 | 23.2 |
| tac3 | ilvA⁻, tdh::Cm, ptacthrABC | Ile, IPTG | 86 | 85.7 | 28.8 |
| 6-8 | ilvA⁻, tdh::Cm, Bor-R | Ile | 70 | 74.1 | 28.3 |
| 6-8tac3 | ilvA⁻, tdh::Cm, ptacthrABC, Bor-R | Ile, IPTG | 75 | 99.3 | 35.1 |
| 6-8tac3ile+ | tdh::Cm, Bor-R, ptacthrABC | IPTG | 62 (at 22 hours) | NA | NA |
| kat13 | tdh::Cm, Bor-R, ptacthrABC lacI⁻ | None | 92.1 | 102 | 33.1 |

Bor-R: borrelidin Resistance
ND: Not done
NA: Not available
ptacthrABC: the thrA, thrB and thrC genes under control of the tac promoter

What is claimed is:

1. A strain of the microorganism E. coli having the following characteristics:

(i) its chromosome contains at least one threonine (thr) operon operably linked with at least one non-native promoter which replaces the native promoter via insertion into said chromosome;

(ii) it does not require any recombinant plasmids containing one or more genes that encode one or more of the threonine biosynthesis enzymes in order to produce threonine; and (iii) it produces L-threonine.

2. The strain of claim 1, wherein said threonine operon consists of a feedback-resistant aspartate kinase I-homoserine dehydrogenase I gene (thrA), a homoserine kinase (thrB) gene, a threonine synthase gene (thrC).

3. The strain according to claim 1, wherein said non-native promoter is the tac promoter.

4. The strain of claim 1, wherein said E. coli contains a defective threonine dehydrogenase gene on the chromosome.

5. The strain of claim 1, wherein said threonine operon is obtained from ATCC 21277.

6. The strain of claim 1, wherein said E. coli is borrelidin resistant.

7. The strain of claim 1, wherein said E. coli has the characteristics of strain NRRL B-21593.

8. The strain of claim 1, wherein said E. coli is capable of producing at least about 50 g/L of L-threonine in about 30 hours.

9. The strain of claim 1, wherein said non-native promoter is selected from the group consisting of the tac promoter, the lac promoter, the trp promoter, the lpp promoter, the P$_L$ promoter and the P$_R$ promoter.

10. The strain of claim 1, wherein said threonine operon contains a gene that encodes a feedback-resistant aspartate kinase-homoserine dehydrogenase.

11. The strain of claim 2, wherein said E. coli is borrelidin resistant.

12. The strain of claim 3, wherein said E. coli is borrelidin resistant.

13. The strain of claim 4, wherein said *E. coli* is borrelidin resistant.

14. The strain of claim 5, wherein said *E. coli* is borrelidin resistant.

15. The strain of claim 9, wherein said *E. coli* is borrelidin resistant.

16. The strain of claim 10, wherein said *E. coli* is borrelidin resistant.

17. The strain of claim 2, wherein said *E. coli* contains a defective threonine dehydrogenase gene on the chromosome.

18. The strain of claim 5, wherein said *E. coli* contains a defective threonine dehydrogenase gene on the chromosome.

19. The strain of claim 9, wherein said *E. coli* contains a defective threonine dehydrogenase gene on the chromosome.

20. The strain of claim 10, wherein said *E. coli* contains a defective threonine dehydrogenase gene on the chromosome.

* * * * *